United States Patent [19]

Soula et al.

[11] Patent Number: 4,578,495

[45] Date of Patent: Mar. 25, 1986

[54] PREPARATION OF ORGANOSILANES/ORGANOPOLYSILANES FROM DISILANES

[75] Inventors: Gerard Soula, Meyzieu; Christian Simonnet, Venissieux, both of France

[73] Assignee: Rhone-Poulenc Specialties Chimiques, Courbevoie, France

[21] Appl. No.: 739,109

[22] Filed: May 30, 1985

[30] Foreign Application Priority Data

May 30, 1984 [FR] France ................................ 8408511

[51] Int. Cl.$^4$ ............................................... C07F 7/08
[52] U.S. Cl. ..................................... 556/468; 556/430
[58] Field of Search ................................ 556/430, 468

[56] References Cited

U.S. PATENT DOCUMENTS 3,576,035 4/1971 Atwell ................................... 556/468
4,291,167 9/1981 Allain et al. ......................... 556/430

Primary Examiner—Paul F. Shaver
Attorney, Agent, or Firm—Burns, Doane, Swecker & Mathis

[57] ABSTRACT

The organosilanes/organopolysilanes, e.g., methylchlorosilanes useful in the production of silicones, are facilely prepared by contacting, in an inert atmosphere, (1) at least one disilane having the general formula:

$$(R)_3 Si-Si-R)_3 \qquad (I)$$

wherein the radicals R, which may be identical or different, are each $C_1$-$C_6$ alkyl, hydrogen, 3,3,3-trifluoropropyl, trimethylsiloxy, fluorine, chlorine, bromine or iodine, with (2) a catalytically effective amount of a catalyst system comprising (a) at least one ionic inorganic salt having the formula:

$$M^+A^-$$

wherein $M^+$ is lithium, sodium, potassium, rubidium or cesium, and $A^-$ is fluoride, chloride, bromide or iodide, and (b) at least one compound which complexes the cation $M^+$ of said salt (a), e.g., a sequestering agent having the formula:

$$N-CHR_1-CHR_2\ O-CHR_3\ CH-R_4\ O)_n\ R_5]_3 \qquad (II).$$

20 Claims, No Drawings

PREPARATION OF ORGANOSILANES/ORGANOPOLYSILANES FROM DISILANES

BACKGROUND OF THE INVENTION

1. Field of the Invention

The present invention relates to an improved process for the preparation of organosilanes and organopolysilanes from organodisilanes.

2. Description of the Prior Art

Various processes for the preparation of organosilanes and/or optionally hydroorganosilanes from organohalodisilanes are already known to this art.

In particular, various methods of processing residues from the direct synthesis of methylchlorosilanes (reaction of methyl chloride with silicon in the presence of copper, described in U.S. Pat. Nos. 2,380,995 and 2,488,487) which consist of mixtures of compounds including, among others, disilanes, are described, for example in French Pat. Nos. 1,093,399, 2,163,579 and 2,163,579.

Thus, according to French Pat. No. 1,093,399, disilanes are cleaved by heating at a temperature of from 200° to 300° C. in the presence of hydrochloric acid.

According to French Pat. No. 2,163,579, a disilane is reacted with a halide in the presence of platinum or palladium, or a phosphine complex of platinum, palladium and nickel.

And according to French Pat. No. 2,342,981, disilanes are reacted with hydrogen gas under pressure in the presence of an aprotic base such as hexamethylphosphoric triamide.

While the known processes indeed enable the preparation of the organosilanes/organopolysilanes, they nevertheless display at least one of the following disadvantages:

(i) the process requires conditions of temperature or pressure which render industrial application difficult and costly;

(ii) the catalysts and/or the reactants employed are toxic, costly and/or unstable in air; and (iii) the reaction time is too long and/or the yields are but mediocre.

SUMMARY OF THE INVENTION

Accordingly, a major object of the present invention is the provision of an improved process for the preparation of organosilanes and polysilanes from organohalodisilanes, which improved process is conspicuously devoid of those disadvantages and drawbacks to date characterizing the state of this art and which is facilely carried out in the absence of gaseous hydrochloric acid, at slightly elevated temperature and at atmospheric pressure, with a short reaction time, with a good yield of organohalosilanes and following a high degree of cleavage of the disilanes.

Briefly, the present invention features a process for the preparation of organosilanes and organopolysilanes by contacting, in an inert atmosphere, at least:

(1) one disilane having the general formula $$(R)_3-Si-Si-(R)_3 \quad (I)$$

in which the radicals R, which are identical or different, denote a hydrocarbon radical selected from among a $C_1-C_6$ alkyl radical, a hydrogen atom, a 3,3,3-trifluoropropyl radical, a trimethylsiloxy radical and a halogen atom selected from among fluorine, chlorine, bromine, and iodine, with (2) a catalytically effective amount of a catalyst system comprising:

(a) at least one ionic inorganic salt having the formula:

in which $M^+$ denotes a cation of an alkali metal selected from among lithium, sodium, potassium, rubidium and cesium and $A^-$ denotes a halide anion selected from among fluoride, chloride, bromide and iodide anion; and (b) at least one compound complexing the $M^+$ cation of the said salt (a).

DETAILED DESCRIPTION OF THE INVENTION

More particularly according to the present invention, in the above formula (I) at least one of the radicals R is preferably a halogen atom, thus preferably excluding the hexahydrocarbon-based disilanes.

Also, preferably in the formula (I) above, on at least one of the two silicon atoms, at least one of the radicals R, and still more preferably at least 2, is a halogen atom.

The process according to the invention is preferably applicable to disilanes of formula (I) in which the radicals R are selected from among the methyl radical and a chlorine atom. These disilanes are well known compounds and, in particular, the above disilanes containing methyl and chloride substituents are present in the residue from the direct synthesis of chlorosilanes.

The disilanes which are preferred according to the invention are tetramethyl-1,2-dichlorodisilane$(Cl(CH_3)_2Si)_2$, trimethyl-1,1,2-trichlorodisilane $CH_3Cl_2SiSiCl(CH_3)_2$, tetrachloro-1,2-dimethyldisilane$(Cl_2CH_3Si)_2$, and tetramethyl-1,1-dichlorodisilane $CH_3Cl_2SiSi(CH_3)_3$ used either alone or in admixture.

These disilanes are found mixed, principally in the fractions of the residue from the direct synthesis which distill at from 151° to 155° C., preferably from 152° to 154° C.

In the catalyst system according to the invention the preferred alkali metal is lithium and the preferred inorganic salts are lithium fluroide, chloride and bromide.

By "insert atmosphere", there is intended that the contacting of the disilanes with the catalyst system is carried out under an inert gas such as argon, nitrogen or helium, under substantially anhydrous conditions. "Substantially anhydrous conditions" are intended to connote a virtually complete absence of moisture, although trace amounts of water can be tolerated.

In the case where the process according to the invention is carried out on a very rich mixture (over approximately 90% molar) of cleavable compounds, a weight yield of monosilanes of from approximately 45 to 85% by weight relative to the weight of the starting material disilanes is typically obtained, the remainder being converted to polysilane principally containing methylchlorosilylene units $CH_3ClSi$.

The silanes obtained are then principally methyltrichlorosilane and dimethyldichlorosilane which are the raw materials essential for the synthesis of silicones.

According to a first and preferred embodiment of the invention, the complexing compound (b) is a sequestering agent having the formula:

$$\text{N—[CHR}_1\text{—CHR}_2\text{—O—CHR}_3\text{—CHR}_4\text{—O)}_n\text{—R}_5]_3 \qquad \text{(II)}$$

in which n is an integer ranging from 0 to 10, inclusive, $R_1$, $R_2$, $R_3$, and $R_4$, which are identical or different, are selected from among a hydrogen atom and a $C_1$-$C_4$ alkyl radical, and $R_5$ is a radical selected from among a $C_1$-$C_{12}$ alkyl or cycloalkyl radical, or an alkylphenyl or phenylalkyl radical in which the alkyl moiety is $C_1$-$C_{12}$.

The complexing agents of formula (II) employed in the subject catalyst system are well known materials which are described, in particular, in French Pat. Nos. 1,302,365 and 2,450,120.

In another preferred embodiment of the invention, a sequestering agent of formula (II) is employed, in which $R_1$, $R_2$, $R_3$ and $R_4$ denote a hydrogen atom or a methyl radical, with $R_5$ and n being as above defined.

Among such latter agents, even more preferred are those sequestering agents in which n is greater than or equal to 0 and smaller than or equal to 6 and in which $R_5$ denotes an alkyl radical containing from 1 to 4 carbon atoms.

Exemplary such sequestering agents include:

[1] Tris(3-oxabutyl)amine having the formula:

$$N(CH_2\text{—}CH_2\text{—}O\text{—}CH_3)_3;$$

[2] Tris(3,6-dioxaheptyl)amine having the formula:

$$N(CH_2\text{—}CH_2\text{—}O\text{—}CH_2\text{—}CH_2\text{—}O\text{—}CH_3)_3;$$

[3] Tris(3,6,9-trioxadecyl)amine having the formula:

$$N(CH_2\text{—}CH_2\text{—}O\text{—}CH_2\text{—}CH_2\text{—}O\text{—}CH_2\text{—}CH_2\text{—}O\text{—}CH_3)_3;$$

[4] Tris(3,6-dioxaoctyl)amine having the formula:

$$N(CH_2\text{—}CH_2\text{—}O\text{—}CH_2\text{—}CH_2\text{—}O\text{—}C_2H_5)_5;$$

[5] Tris(3,6,9-trioxaundecyl)amine having the formula:

$$N(CH_2\text{—}CH_2\text{—}O\text{—}CH_2\text{—}CH_2\text{—}O\text{—}CH_2\text{—}CH_2\text{—}O\text{—}C_2H_5)_3;$$

[6] Tris(3,6-dioxanonyl)amine having the formula:

$$N(CH_2\text{—}CH_2\text{—}O\text{—}CH_2\text{—}CH_2\text{—}O\text{—}C_3H_7)_3;$$

[7] Tris(3,6,9-trioxadodecyl)amine having the formula:

$$N(CH_2\text{—}CH_2\text{—}O\text{—}CH_2\text{—}CH_2\text{—}O\text{—}CH_2\text{—}CH_2\text{—}O\text{—}C_3H_7)_3;$$

[8] Tris(3,6-dioxadecyl)amine having the formula:

$$N(CH_2\text{—}CH_2\text{—}O\text{—}CH_2\text{—}CH_2\text{—}O\text{—}C_4H_9)_3;$$

[9] Tris(3,6,9-trioxatridecyl)amine having the formula:

$$N(CH_2\text{—}CH_2\text{—}O\text{—}CH_2\text{—}CH_2\text{—}O\text{—}CH_2\text{—}CH_2\text{—}O\text{—}C_4H_9)_3;$$

[10] Tris(3,6,9,12-tetraoxatridecyl)amine having the formula:

$$N\text{—}(CH_2\text{—}CH_2\text{—}O(CH_2\text{—}CH_2\text{—}O)_3\text{—}CH_3)_3;$$

[11] Tris(3,6,9,12,15,18-hexaoxanonadecyl)amine having the formula:

$$N(CH_2\text{—}CH_2\text{—}O\text{—}(CH_2\text{—}CH_2\text{—}O)_5CH_3)_3;$$

[12] Tris(3,6-dioxa-4-methylheptyl)amine having the formula:

$$N(CH_2\text{—}CH_2\text{—}OCH\text{—}(CH_3)\text{—}CH_2\text{—}O\text{—}CH_3)_3;$$

[13] Tris(3,6-dioxa-2,4-dimethylheptyl)amine having the formula:

$$N\text{—}(CH_2CH\text{—}(CH_3)\text{—}OCH(CH_3)\text{—}CH_2\text{—}O\text{—}CH_3)_3.$$

In another preferred embodiment of the invention, sequestering agents grafted onto cross-linked organic polymer substrates are employed as the complexing compound. These grafted complexing compounds are especially those described in published European Patent Application No. 46,706.

The grafted sequestering agents described in said published European Patent Application No. 46,706 are characterized in that they consist of a cross-linked organic polymer substrate and a plurality of functional groups affixed to said substrate, and having the general formula:

$$N \begin{cases} \text{—}(CHR'_1\text{—}CHR'_2\text{—}O)_{n'}\text{—} \\ \text{—}(CHR'_3\text{—}CHR'_4\text{—}O)_{m'}\text{—}R'_5 \\ \text{—}(CHR'_6\text{—}CHR'_7\text{—}O)_{p'}\text{—}R'_8 \end{cases} \qquad \text{(III)}$$

in which $R'_1$, $R'_2$, $R'_3$, $R'_4$, $R'_6$ and $R'_7$, which are identical or different, are selected from among a hydrogen atom and an alkyl radical containing from 1 to 4 carbon atoms, $R'_5$ and $R'_8$, which are identical or different, are selected from among a hydrogen atom, an alkyl or cycloalkyl radical containing from 1 to 12 carbon atoms, a phenyl radical, an alkylphenyl or phenylalkyl radical in which the alkyl moiety is $C_1$-$C_{12}$ and in which n', m', and p', which are identical or different, are greater than or equal to 1 and less than or equal to 10.

It would appear, although we do not wish to be bound to this theory, that the invention is based on the fact that the complexing agent complexes the $M^+$ cation of the ionic inorganic salt and permits the dissociation and at least partial solubilization of the salt in the reaction medium.

According to another preferred embodiment of the invention, a supported sequestering agent is used consisting of a cross-linked organic polymer substrate having a plurality of functional groups affixed to said substrate, and having the general formula (III) in which $R'_1$, $R'_2$, $R'_3$, $R'_4$, $R'_6$, and $R'_7$, which are identical or different, denote a hydrogen atom, or the methyl radical and $R'_5$ and $R'_8$, which are identical or which are identical or different, denote a hydrogen atom or a $C_1$-$C_4$ alkyl radical. In yet another preferred embodiment of the invention, n', m' and p', which are identical or different, are greater than or equal to 1 and less than or equal to 6.

Exemplary of such functional groups, the following are representative:

$$N \begin{cases} \text{CH}_2\text{—}CH_2\text{—}O\text{—} \\ \text{CH}_2\text{—}CH_2\text{—}O\text{—}CH_3 \\ \text{CH}_2\text{—}CH_2\text{—}O\text{—}CH_3 \end{cases}$$

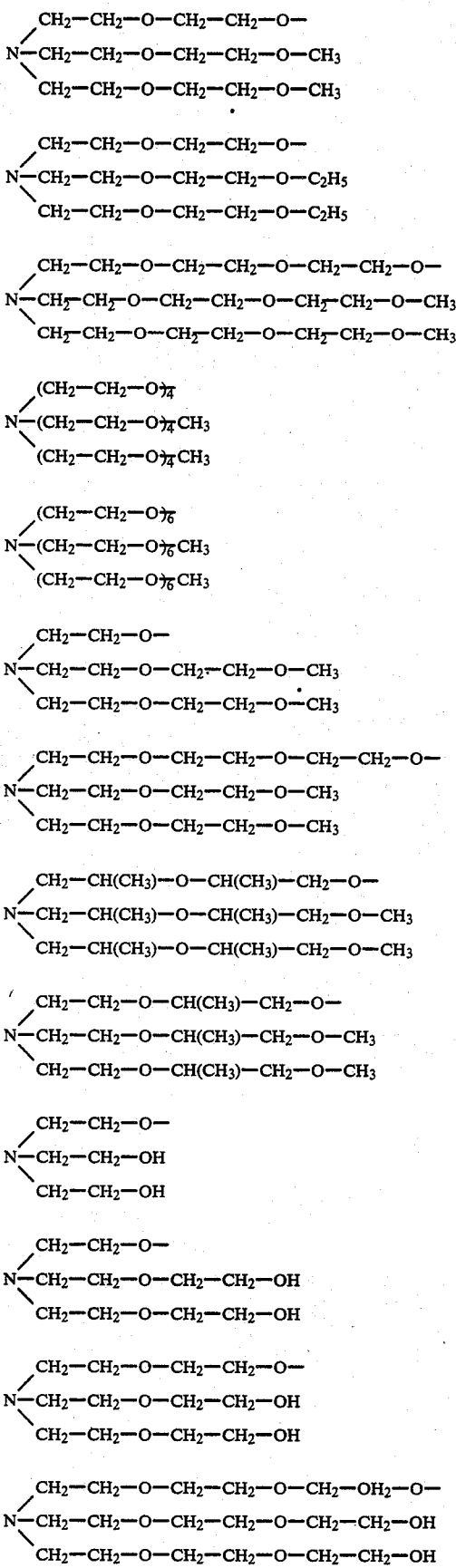

The substrate may be derived from any cross-linked organic polymer containing groups replaceable by the said functional groups having the formula (III).

Exemplary of organic polymers suitable for the present invention, representative are polymers derived from vinylaromatic compounds such as styrene and methylstyrene, and copolymers of vinylaromatic compounds with $C_4$-$C_6$ conjugated dienes, such as copolymers of styrene with butadiene and of styrene with isoprene.

The organic polymer employed which is the most preferred is polystyrene, the cross-linking agent then being, according to another preferred embodiment, divinylbenzene. The degree of cross-linking is an important factor. The functional groups of formula (III) which are grafted onto the polystyrene must, in fact, be active. For this to be so, it is necessary for the molecules of the solvent, in which the supported sequestering agent will be employed (in the applications which will be detailed hereinafter) to penetrate inside the polymer. To this end, the degree of cross-linking must not be too high such that it will not prevent the entry of the solvent and the reactants. It is preferred to employ a polystyrene whose degree of cross-linking by divinylbenzene is below approximately 10%. Still more preferably, the degree of cross-linking is below approximately 5%.

The replaceable group is preferably chlorine or bromine in the chloro- or bromomethyl radical, —$CH_2Cl$ or —$CH_2Br$, attached to the benzene nucleus of the polystyrene.

It is especially preferable that the percentage of the benzene nuclei in the polystyrene which bear a functional group be greater than 5%. Still more preferably, this percentage is greater than 10%.

Exemplary of the preferred support sequestering agents, those of the following formula are representative:

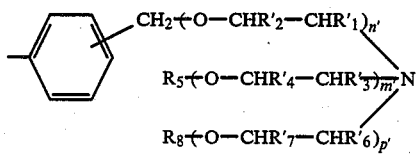

In a second preferred embodiment of the invention, the complexing compound (b) is a macrocyclic polyether containing from 15 to 30 atoms in the ring and consisting of 4 to 10 —O—X units, in which X is either —$CHR_6$—$CHR_7$— or —$CHR_6$—$CHR_8$—$CR_9R_7$—, $R_6$, $R_7$, $R_8$ and $R_9$, which are identical or different, being a hydrogen atom or an alkyl radical containing from 1 to 4 carbon atoms, one X being capable of being —$CHR_6$—$CHR_8$—$CR_9R_7$— when the O—X units contain the group —O—$CHR_6$—$CHR_7$.

In a third preferred embodiment of the invention, the complexing compound (b) is a macrocyclic or bicyclic compound having the general formula IIa or IIb:

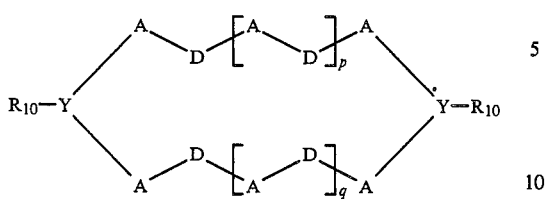
(IIa)

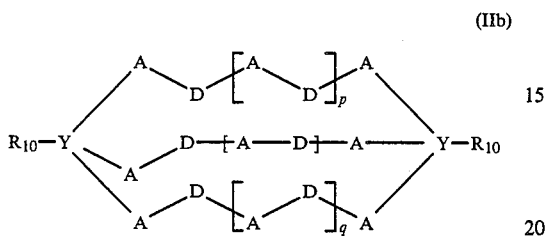
(IIb)

in which Y denotes N or P; A denotes an alkylene group containing from 1 to 3 carbon atoms; D denotes O, S or N—$R_{11}$, where $R_{11}$ denotes an alkyl radical containing from 1 to 6 carbon atoms; $R_{10}$ denotes an alkyl radical containing from 1 to 6 carbon atoms, and p, q and r, which are identical or different, are integers ranging from 1 to 5.

In a fourth preferred embodiment of the invention, the complexing compound (b) is a macrocyclic polyether (also designated "crown ether") or a macrocyclic or bicyclic compound (also designated "cryptant") which are grafted onto cross-linked organic polymer substrates. These grafted complexing compounds are especially those described in *Angew. Chem. Int. Ed. Eng.*, 18, 421–429 (1979) when the compounds in question are crown ethers or grafted cryptants.

The macrocyclic polyethers which may be employed in the process according to the invention are generally known to this art as "crown ethers" and are described, for example, in French Patent Application No. 69/43879, published under No. 2,026,481.

The following are exemplary of the crown ethers which can be employed according to the invention:

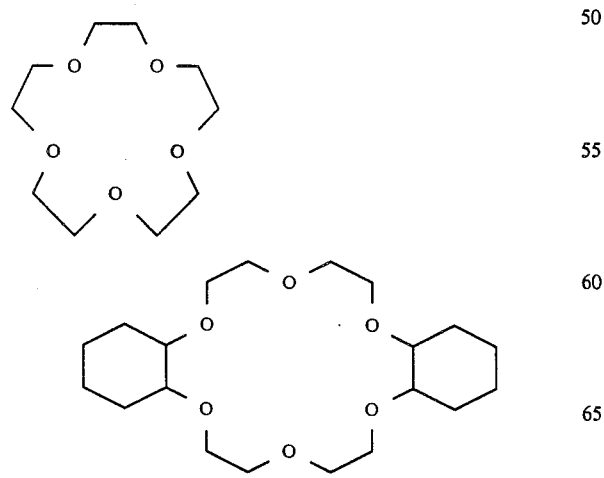

The macrocyclic and bicyclic compounds are described in French Patent Application No. 70/21079, published under No. 2,052,947. The following are exemplary of such compounds which are useful according to the invention:

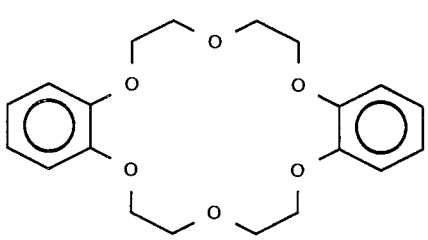

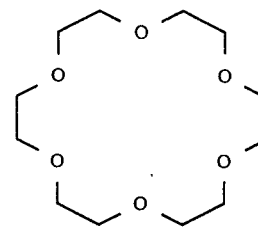

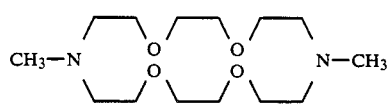

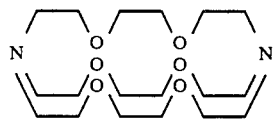

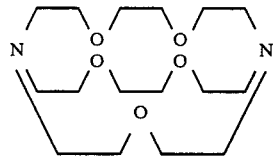

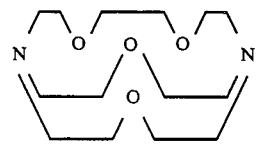

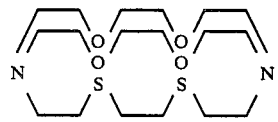

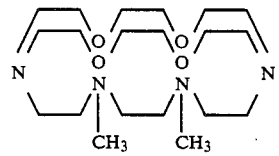

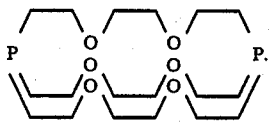

In another preferred embodiment of the invention, the compound (b) is a macrocyclic polyether or a macrocyclic or bicyclic compound grafted onto a cross-linked organic polymer which consists of a polystyrene obtained by reacting the appropriate amine derivative, macrocyclic polyether or macrocyclic or bicyclic compound with a chloromethylated polystyrene. These preferred supported materials may be represented by the following formulae:

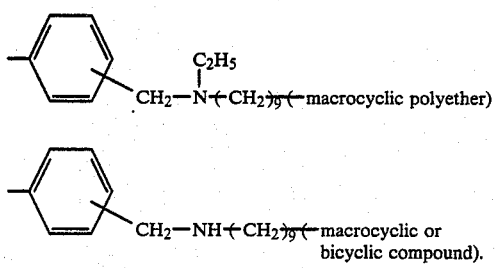

The process according to the invention may be carried out in the presence or absence of solvent. In the latter case, it is the starting material disilane or mixture of disilanes which serves as a solvent. When a third solvent is employed, the latter must meet a number of conditions: it must solubilize the starting material disilane; it must also be chemically inert versus the silanes and polysilanes which are introduced or formed.

Preferably, a solvent such as, for example, anisole, chlorobenzene, ortho-dichlorobenzene, toluene, dichlorobenzene, dioxane, or dimethoxyethane is selected. Anisole and chlorobenzene are the preferred solvents.

The selection of the sequestering agent of formula (II) which is the most suitable for use in the process according to the invention is made, moreover, by taking into account the size of the cation in the ionic inorganic salt. The greater the size of the cation, the higher must be the number of oxygen atoms present in the molecule of sequestering agent.

The process according to the invention is preferably carried out at a temperature of from 80° to 200° C., preferably from 100° to 150° C.; this constitutes one of the advantages of the process according to the invention.

The process is preferably carried out at atmospheric pressure. Pressures greater than or lower than atmospheric pressure are, of course, not excluded.

The complexing agent (b) is employed in a quantity such that the molar ratio of the complexing agent to the ionic inorganic salt preferably ranges from 0.001 to 10. More preferably, such ratio ranges from 0.02 to 2.

The molar ratio of the ionic inorganic salt to the starting material disilane preferably ranges from 1 to 0.001. More preferably, it ranges from 0.5 to 0.01.

The silanes obtained by the scission reaction may either be separated as they are formed when they are poorly soluble in the reaction medium and are sufficiently volatile, or separated upon completion of reaction in accordance with techniques which are well known to this art, such as, for example, distillation, selective dissolution, and the like.

The grafted complexing agents according to the invention make it possible to carry out the process, preferably continuously, in a column, while the ungrafted complexing agents make it possible to operate preferably noncontinuously.

The present invention thus makes it possible to cleave the disilanes at a slightly elevated temperature and with an outstanding yield, while employing but small quantities of catalyst.

In order to further illustrate the present invention and the advantages thereof, the following specific examples are given, it being understood that same are intended only as illustrative and in nowise limitative.

EXAMPLE 1

Into a 1 liter reactor fitted with central stirrer, thermometer, a column packed with Raschig rings, condenser, receiver and argon inlet, where charged 150 g of disilanes consisting of:

(i) 0.198 mole of trimethyl-1,1,2-trichlorodisilane;
(ii) 0.439 mole of tetrachloro-1,2-dimethyldisilane;
(iii) 7.5 g, i.e., 0.0230 mole of tris(3,6-dioxaheptyl)amine, hereinafter designated T $DA_1$; and
(iv) 1 g of anhydrous lithium fluoride, i.e., 0.0384 mole.

The entire mass was stirred while heat was applied and appreciable quantities of monosilanes ($Cl_2Si(CH_3)_2$ and $CH_3SiCl_3$) began to distill off at about 110° C. in the reactor. The reaction was terminated after 9 minutes, as the temperature in the reactor reached 150° C. A solid residue principally consisting of polymethylchlorosilanes was obtained from the base of the reactor. The weight yield of monosilanes relative to the weight of the disilanes introduced (degree of scission) was 55.6%. Based on the weight of disilanes cleaved, the weight yield of methylchlorosilane was 79.6% and that of dimethyldichlorodisilane was 87.6%.

EXAMPLES 2 TO 9

The operating procedure of Example 1 was repeated with the same number of moles of reactant and of catalyst system, except that the nature of the alkali metal halide was changed. The results obtained are reported in Table I below. From this table, it will be seen that the systems T $DA_1$+LiBr or LiCl or LiF were the most active.

Example 9 is a comparative example demonstrating that the presence of a sequestering agent is essential in the catalyst system.

TABLE I

| Ex. | Catalyst | Time in hr and min | Weight degree of scission % | Weight yield of $SiCl_3$ % | Weight yield of $(CH_3)_2SiCl_2$ % |
|---|---|---|---|---|---|
| 1 | T $DA_1$ + LiF | 9 min | 55.6 | 79.6 | 87.6 |
| 2 | T $DA_1$ + LiCl | 11 min | 51 | 64 | 88.8 |
| 3 | T $DA_1$ + Nacl | 2 hr, 55 min | 53.3 | 82 | 87.5 |

TABLE I-continued

| Ex. | Catalyst | Time in hr and min | Weight degree of scission % | Weight yield of SiCl$_3$ % | Weight yield of (CH$_3$)$_2$SiCl$_2$ % |
|---|---|---|---|---|---|
| 4 | T DA$_1$ + LiBr | 14 min | 58 | 84.9 | 93.2 |
| 5 | T DA$_1$ + LiI | 21 min | 50 | 66.3 | 89 |
| 6 | T DA$_1$ + NaF | 3 hr, 15 min | 48.6 | 68.7 | 85.4 |
| 7 | T DA$_1$ + KF | 4 hr, 05 min | 48.6 | 70.6 | 82.9 |
| 8 | T DA$_1$ + NaI | 3 hr | 14.6 | 16.80 | 35.4 |
| 9 | LiCl | 4 hr | 0 | 0 | 0 |

EXAMPLE 10

The operating procedure of Example 1 was repeated except that 200 ml of anisole were charged into the reactor beforehand.

The results obtained were essentially identical to those obtained in Example 1 when the process was carried out without a solvent.

EXAMPLES 11 TO 14

In these examples, the process of the invention was carried out continuously in a 1 liter glass reactor maintained under stirring and incorporating a system for continuous disilane feed, a system for continuous withdrawal of the liquid phase and a distillation column packed with Raschig ® rings, with a variable reflux ratio.

The disilane mixture continuously fed had the following composition by weight:
(i) 1,2-dimethyltetrachlorodisilane: 46.6%
(ii) 1,1,2-trimethyltrichlorodisilane: 39.3%
(iii) other disilanes: 14.1%

The catalyst (alkali metal halide dissolved in T DA$_1$) was introduced mixed with the disilanes.

In Examples 11 to 14, the following conditions were modified:
Ex. 11 and 12: nature of the halide (fluoride and chloride);
Ex. 12, 13 and 14: residence time, temperature in the reactor and column reflux ratio.

The operating conditions and results obtained are reported in Table II below:

| Examples | 11 | 12 | 13 | 14 |
|---|---|---|---|---|
| Catalyst system | LiF/T DA$_1$ | LiCl/T DA$_1$ | LiCl/T DA$_1$ | LiCl/T DA$_1$ |
| Weight % catalyst W/W (1) | 0.5 | 0.5 | 0.5 | 0.5 |
| LiX/T DA$_1$ (2) | 0.10 | 0.03 | 0.03 | 0.03 |
| Temperature (°C.) | 160 | 160 | 170 | 160 |
| Residence time (hr) | 1.75 | 2.17 | 2.05 | 3.00 |
| Column reflux ratio | | 0.3/1 | 1.3/1 | 2/1 |
| Output (per hour) | | | | |
| Kg Me$_2$SiCl$_2$ per kg of disilanes reacted | 0.230 | 0.190 | 0.205 | 0.202 |
| Kg MeSiCl$_3$ per kg of disilanes reacted | 0.384 | 0.342 | 0.388 | 0.375 |
| Kg Me$_3$SiCl per kg of disilanes reacted | 0.007 | 0.010 | 0.011 | 0.011 |
| Kg MeHSiCl$_2$ per kg of disilanes reacted | 0.001 | 0.002 | 0.002 | 0.002 |
| Kg organosilanes per kg of disilanes reacted | 0.622 | 0.544 | 0.606 | 0.590 |
| Weight % of disilanes and polydisilanes in the distilled products relative to the total weight of all products | 5.8 | 1.5 | 0.27 | 0.23 |

| | 11 | 12 | 13 | 14 |
|---|---|---|---|---|
| obtained | | | | |

(1) Weight % of the catalyst system relative to the total weight of the reaction mixture in the reactor (including the weight of the catalyst system)
(2) Weight ratio While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of organosilane/polysilane, comprising comprising contacting, in an inert atmosphere, (1) at least one disilane having the general formula:

$$(R)_3 Si-Si-R)_3 \qquad (I)$$

wherein the radicals R, which may be identical or different, are each C$_1$–C$_6$ alkyl, hydrogen, 3,3,3-trifluoropropyl, trimethylsiloxy, fluorine, chlorine, bromine or iodine, with (2) a catalytically effective amount of a catalyst system comprising (a) at least one ionic inorganic salt having the formula:

$$M^+ A^-$$

wherein M$^+$ is lithium, sodium, potassium, rubidium or cesium, and A$^-$ is fluoride, chloride, bromide or iodide, and (b) at least one compound which complexes the cation M$^+$ of said salt (a).

2. The process as defined by claim 1, said complexing compound (b) comprising a sequestering agent having the formula:

$$N-CHR_1-CHR_2 \quad O-CHR_3 \quad CH-R_4 \quad O)_n \quad R_5]_3 \qquad (II)$$

wherein n is an integer ranging from 0 to 10, R$_1$, R$_2$, R$_3$ and R$_4$, which may be identical or different, are each hydrogen or C$_1$–C$_4$ alkyl, and R$_5$ is C$_1$–C$_{12}$ alkyl or cycloalkyl, or alkylphenyl or phenylalkyl in which the alkyl moiety is C$_1$–C$_{12}$.

3. The process as defined by claim 1, said complexing compound (b) comprising a macrocyclic polyether containing from 15 to 30 ring atoms and 4 to 10 —O—X units, in which X is —CHR$_6$—CHR$_7$— or —CHR$_6$—CHR$_8$—CR$_9$R$_7$—, wherein R$_6$, R$_7$, R$_8$ and R$_9$, which may be identical or different, are each hydrogen or C$_1$–C$_4$ alkyl, with the proviso that one X can be —CHR$_6$—CHR$_8$—CR$_9$R$_7$— when the —O—X units comprise —O—CHR$_6$—CHR$_7$—.

4. The process as defined by claim 1, said complexing compound (b) comprising a macrocyclic or bicyclic compound having the general formula IIa or IIb:

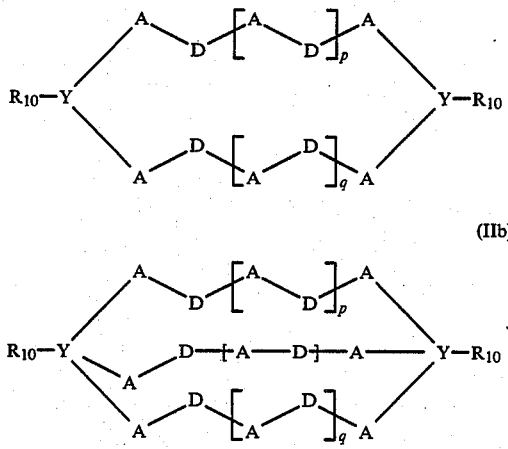

(IIa)

(IIb)

wherein Y is N or P, A is $C_1$-$C_3$ alkylene, D is O, S or N—$R_{11}$, in which $R_{11}$ is $C_1$-$C_6$ alkyl, $R_{10}$ is $C_1$-$C_6$ alkyl, and p, q and r, which may be identical or different, are each an integer of from 1 to 5.

5. The process as defined in claim 1, said complexing compound (b) comprising a sequestering agent, macrocyclic polyether or macrocyclic or bicyclic compound grafted onto a cross-linked organic polymer substrate.

6. The process as defined in claim 1, wherein at least one R comprising said at least one disilane (I) is a halogen.

7. The process as defined in claim 1, wherein the at least one disilane (I), each R is methyl or chlorine.

8. The process as defined in claim 1, said at least one disilane (I) comprising tetramethyl-1,2-dichlorodisilane, trimethyl-1,1,2-trichlorodisilane, tetrachloro-1,2-dimethyldisilane or tetramethyl-1,1-dichlorodisilane.

9. The process as defined by claim 1, wherein said salt (a), M+ is lithium.

10. The process as defined by claim 9, said salt (a) comprising lithium fluoride, chloride or bromide.

11. The process as defined by claim 2, wherein said sequestering agent (II), $R_1$, $R_2$, $R_3$ and $R_4$ are each hydrogen or methyl, n ranges from 0 to 6, and $R_5$ is $C_1$-$C_4$ alkyl.

12. The process as defined in claim 2, wherein said sequestering agent (II) is grafted onto a cross-linked organic polymer substrate and comprises a plurality of functional groups of the general formula:

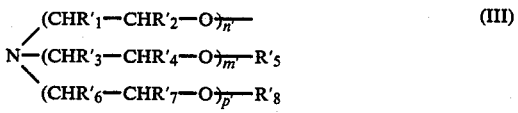

(III)

wherein $R'_1$, $R'_2$, $R'_3$, $R'_4$, $R'_6$ and $R'_7$, which may be identical or different, are each hydrogen or $C_1$-$C_4$ alkyl, $R'_5$ and $R'_8$, which may be identical or different, are each hydrogen, $C_1$-$C_{12}$ alkyl or cycloalkyl, phenyl, phenylalkyl or alkylphenyl radical in which the alkyl moiety is $C_1$-$C_{12}$ alkyl, and n', m' and p', which may be identical or different, are each greater than or equal to 1 and less than or equal to 10.

13. The process as defined by claim 12, wherein said functional groups (III), $R'_1$, $R'_2$, $R'_3$, $R'_4$, $R'_6$ and $R'_7$, which may be identical or different, are each hydrogen or methyl, $R'_5$ and $R'_8$, which may be identical or different, are each hydrogen or $C_1$-$C_4$ alkyl, and n', m' and p', which may be identical or different, each range from 1 to 6.

14. The process as defined by claim 1, said contacting being in an organic solvent which is chemically inert towards silanes and polysilanes which are introduced or formed.

15. The process as defined by claim 14, said solvent comprising anisole or chlorobenzene.

16. The process as defined by claim 1, said contacting being at a temperature ranging from 80° to 200° C.

17. The process as defined by claim 1, the molar ratio of said ionic inorganic salt (a) to the starting material disilane (1) ranging from 1 to 0.001, and the molar ratio of said complexing compound (b) to the ionic inorganic salt (a) ranging from 0.001 to 10.

18. The process as defined by claim 1, said complexing compound (b) comprising a crown ether.

19. The process as defined by claim 1, said complexing compound (b) comprising a cryptant grafted onto a cross-linked orgnanic polymer substrate.

20. The process as defined by claim 6, wherein at least two R's comprising said at least one disilane (I) are halogens.

* * * * *